United States Patent
Suzuki et al.

(10) Patent No.: US 7,217,244 B2
(45) Date of Patent: May 15, 2007

(54) PRESSURE PULSE WAVE SENSOR AND PRESSURE-PULSE-WAVE ANALYZING APPARATUS

(75) Inventors: Hidenori Suzuki, Nagoya (JP); Akio Yamanishi, Kawabe-gun (JP)

(73) Assignee: Omron Healthcare Co., Ltd., Kyoto (JP)

( * ) Notice: Subject to any disclaimer, the term of this patent is extended or adjusted under 35 U.S.C. 154(b) by 567 days.

(21) Appl. No.: 10/729,906

(22) Filed: Dec. 9, 2003

(65) Prior Publication Data

US 2005/0038347 A1    Feb. 17, 2005

(30) Foreign Application Priority Data

Dec. 26, 2002   (JP)  ............................. 2002-378309

(51) Int. Cl.
    *A61B 5/00*    (2006.01)
(52) U.S. Cl. ....................... 600/500; 600/481
(58) Field of Classification Search .................... None
    See application file for complete search history.

(56) References Cited

U.S. PATENT DOCUMENTS

| | | | | |
|---|---|---|---|---|
| 4,561,447 A | * | 12/1985 | Kawamura et al. | ......... 600/500 |
| 4,784,152 A | * | 11/1988 | Shinoda et al. | ............. 600/503 |
| 4,960,118 A | * | 10/1990 | Pennock | ................. 128/200.24 |
| 5,617,868 A | * | 4/1997 | Harada et al. | ............... 600/490 |
| 5,792,058 A | * | 8/1998 | Lee et al. | .................... 600/459 |
| 6,033,370 A | * | 3/2000 | Reinbold et al. | ........... 600/595 |
| 6,491,647 B1 | * | 12/2002 | Bridger et al. | .............. 600/585 |
| 2003/0115966 A1 | * | 6/2003 | Ueno et al. | .................... 73/726 |

FOREIGN PATENT DOCUMENTS

| JP | A-57-122844 | 7/1982 |
|---|---|---|
| JP | A-06-197873 | 7/1994 |
| JP | A-2000-051164 | 2/2000 |
| JP | B2 3062202 | 4/2000 |

* cited by examiner

*Primary Examiner*—Charles A. Marmor, II
*Assistant Examiner*—Karen E Toth
(74) *Attorney, Agent, or Firm*—Oliff & Berridge, PLC

(57) ABSTRACT

A pressure pulse wave sensor for being worn on a surface of a body of a living subject so as to detect a pressure pulse wave from the subject, the sensor including a plurality of elongate flexible piezoelectric sheets each of which is formed of a piezoelectric resin and detects a pressure pulse wave from the subject, and a flexible sheet to which the piezoelectric sheets are fixed such that the piezoelectric sheets are arranged in a widthwise direction thereof.

3 Claims, 7 Drawing Sheets

PRESSURE PULSE WAVE SENSOR AND PRESSURE-PULSE-WAVE ANALYZING APPARATUS

BACKGROUND OF THE INVENTION

1. Field of the Invention

The present invention relates to a pressure pulse wave sensor that detects a pressure pulse wave from a body surface of a living being and particularly to such a pressure pulse wave sensor that includes a two-dimensional pressure sensing portion for detecting a pressure pulse wave, and also to an analyzing apparatus that analyzes a pressure pulse wave detected by a pressure pulse wave sensor.

2. Related Art Statement

There is known a pressure pulse wave sensor that is worn on a body surface of a living being and detects a pressure pulse wave from the body surface. For example, there is a pressure pulse wave sensor including a two-dimensional, pressure sensing portion. (cf. Patent Document 1 (Japanese Patent No. 3062202)). In the case where the pressure pulse wave sensor that detects the pressure pulse wave from the body surface is used, it is needed to place the pressure sensing portion of the sensor at a position right above a target-signal producing portion such as an artery. In the case where a pressure sensing portion has a linear shape, a range in which a pressure pulse wave sensor including the sensing portion can be suitably worn is narrow and accordingly it is considerably difficult to locate the sensor at an appropriate position. In contrast, in the case where a pressure sensing portion has a two-dimensional shape, a range in which a pressure pulse wave sensor including the sensing portion can be suitably worn is wide and accordingly it is easy to locate the sensor at an appropriate position.

However, the sensor disclosed by Patent Document 1 has a problem that a press surface of the sensor is defined by a surface of a substrate formed of a monocrystalline silicon and accordingly the press surface has difficulty in fitting a curved shape of a body surface of a living being. Therefore, an accuracy of a pulse wave detected by each of pressure sensing elements arranged in the press surface (i.e., the pressure sensing portion) is not sufficiently high.

SUMMARY OF THE INVENTION

It is therefore an object of the present invention to provide a pressure pulse wave sensor that can obtain an accurate pulse wave from a body surface of a living being, and a pressure pulse wave analyzing apparatus.

The above object has been achieved by the present invention. According to a first aspect of the present invention, there is provided a pressure pulse wave sensor for being worn on a surface of a body of a living subject so as to detect a pressure pulse wave from the subject, the sensor comprising a plurality of elongate flexible piezoelectric sheets each of which is formed of a piezoelectric resin and detects a pressure pulse wave from the subject; and a flexible sheet to which the piezoelectric sheets are fixed such that the piezoelectric sheets are arranged in a widthwise direction thereof.

According to this aspect, the plurality of piezoelectric sheets are flexible and are integrally fixed to the flexible sheet. Therefore, the piezoelectric sheets can be worn on a body surface in the state in which each of the sheets fits a curved shape of the body surface. Thus, each of the piezoelectric sheets can detect a pressure pulse wave accurately representing the displacement of the body surface. On the other hand, a single large piezoelectric sheet having a large area equal to an area defined by the plurality of piezoelectric sheets connected to each other, detects a pulse wave representing a total amount of displacement of the large area. In the latter case, the pulse wave detected is likely to represent other displacements than a target pulse wave produced by a target-signal producing portion. In contrast, the pressure pulse wave sensor according to this aspect employs the plurality of elongate piezoelectric sheets arranged in the widthwise direction thereof, and accordingly each of the piezoelectric sheets detects the displacement of the narrower area than the single large piezoelectric sheet does. Therefore, the piezoelectric sheet located at the position right above the pulse-wave producing portion can detect the pulse wave more accurately representing the target pulse wave produced by the target-signal producing portion.

Here, preferably, the flexible sheet is expansible and contractible. According to this feature, the flexible sheet easily fits the curved shape of the body surface. Thus, the piezoelectric sheets that are fixed to the flexible sheet and are pressed against the body surface more suitably fit the curved shape of the body surface. Therefore, each of the piezoelectric sheets can detect a more accurate pressure pulse wave.

According to a second aspect of the present invention, there is provided a pressure pulse wave sensor for being pressed against a surface of a body of a living subject so as to detect a pressure pulse wave from the subject, the sensor comprising a plurality of elongate flexible piezoelectric sheets each of which is formed of a piezoelectric resin and detects a pressure pulse wave from the subject; and an elastic base member to which the piezoelectric sheets are fixed such that the piezoelectric sheets are arranged in a widthwise direction thereof.

According to this aspect, the plurality of piezoelectric sheets are flexible. In addition, in the state in which the pressure pulse wave sensor is worn on the body surface, each of the piezoelectric sheets is pressed toward the body surface by an elastic, shape recovery force of the elastic base member. Thus, each of the piezoelectric sheets fits the curved shape of the body surface. Therefore, each of the piezoelectric sheets detects a pulse wave accurately representing the displacement of the body surface and the change in pressure in the subject's tissue. On the other hand, a single large piezoelectric sheet having a large area equal to an area defined by the piezoelectric sheets connected to each other, detects a pulse wave representing a total amount of displacement of the large area. In the latter case, the pulse wave detected is likely to represent other displacements than a target pulse wave produced by a target-signal producing portion. In contrast, the pressure pulse wave sensor according to this aspect employs the elongate piezoelectric sheets arranged in the widthwise direction thereof, and accordingly each of the piezoelectric sheets detects the displacement of the narrower area than the single large piezoelectric sheet does. Therefore, the piezoelectric sheet located at the position right above the pulse-wave producing portion can detect the pulse wave more accurately representing the target pulse wave produced by the target-signal producing portion.

According to a third aspect of the present invention, there is provided a pressure-pulse-wave analyzing apparatus that processes the pressure pulse wave detected by each of the piezoelectric sheets of the pressure pulse wave sensor according to the first or second aspect of the present invention, so as to remove noise from the pulse wave and thereby obtain a more accurate pulse wave. The pressure-pulse-wave analyzing apparatus comprises a pressure pulse wave sensor according to the first or second aspect of the present invention; and a noise removing means for subtracting, from one of the respective pressure pulse waves detected by the piezoelectric sheets that has a greatest amplitude of respective amplitudes of the pressure pulse waves, a different one of the pressure pulse waves that is different from the one pressure pulse wave, and thereby removing noise from the one pressure pulse wave.

Since noise such as motion of a muscle is similarly detected in a wide range, the respective pressure pulse waves detected by the respective piezoelectric sheets contain a similar amount of noise. Therefore, if, from the pressure pulse wave having the greatest amplitude, i.e., the pressure pulse wave containing the greatest amount of target-signal component, a pressure pulse wave detected by a different piezoelectric sheet than the piezoelectric sheet detecting the greatest-amplitude pressure pulse wave is subtracted, then noise is removed from the greatest-amplitude pressure pulse wave and accordingly a pulse wave freed of noise can be obtained.

According to a fourth aspect of the present invention, there is provided a pressure-pulse-wave analyzing apparatus, comprising a pressure pulse wave sensor which is adapted to be worn on a surface of a body of a living subject so as to detect a pressure pulse wave from the subject and which comprises a first sensing portion including a plurality of elongate flexible piezoelectric sheets each of which is formed of a piezoelectric resin and detects a first pressure pulse wave from the subject and which are arranged in a widthwise direction thereof, and a second sensing portion including a plurality of elongate flexible piezoelectric sheets each of which is formed of a piezoelectric resin and detects a second pressure pulse wave from the subject and which are arranged in a widthwise direction thereof, the second sensing portion being stacked on the first sensing portion such that the piezoelectric sheets of the second sensing portion extend perpendicularly to the piezoelectric sheets of the first sensing portion; and a synthesizing means for synthesizing a synthetic pulse wave based on one of the respective first pressure pulse waves detected by the piezoelectric sheets of the first sensing portion that has a greatest amplitude of respective amplitudes of the first pressure pulse waves, and one of the respective second pressure pulse waves detected by the piezoelectric sheets of the second sensing portion that has a greatest amplitude of respective amplitudes of the second pressure pulse waves.

According to this aspect, the synthesizing means synthesizes the synthetic pulse wave based on the pulse wave containing the greatest amount of target-signal component of the respective amounts of target-signal components contained by the respective pulse waves detected by the piezoelectric sheets of the first sensing portion, and the pulse wave containing the greatest amount of target-signal component of the respective amounts of target-signal components contained by the respective pulse waves detected by the piezoelectric sheets of the second sensing portion. Therefore, the synthetic pulse wave accurately represents the target pulse wave produced by the target-signal producing portion.

Here, preferably, the pressure-pulse-wave analyzing apparatus further comprises a noise removing means for subtracting, from the one first pressure pulse wave having the greatest amplitude, a different one of the first pressure pulse waves that is different from the one first pressure pulse wave, and thereby removing noise from the one first pressure pulse wave, and subtracting, from the one second pressure pulse wave having the greatest amplitude, a different one of the second pressure pulse waves that is different from the one second pressure pulse wave, and thereby removing noise from the one second pressure pulse wave, and the synthesizing means synthesizes the synthetic pulse wave based on the one first pressure pulse wave from which noise has been removed by the noise removing means and the one second pressure pulse wave from which noise has been removed by the noise removing means. According to this feature, the synthetic pulse wave more accurately represents the target pulse wave.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF PREFERRED EMBODIMENTS

Figure 1:
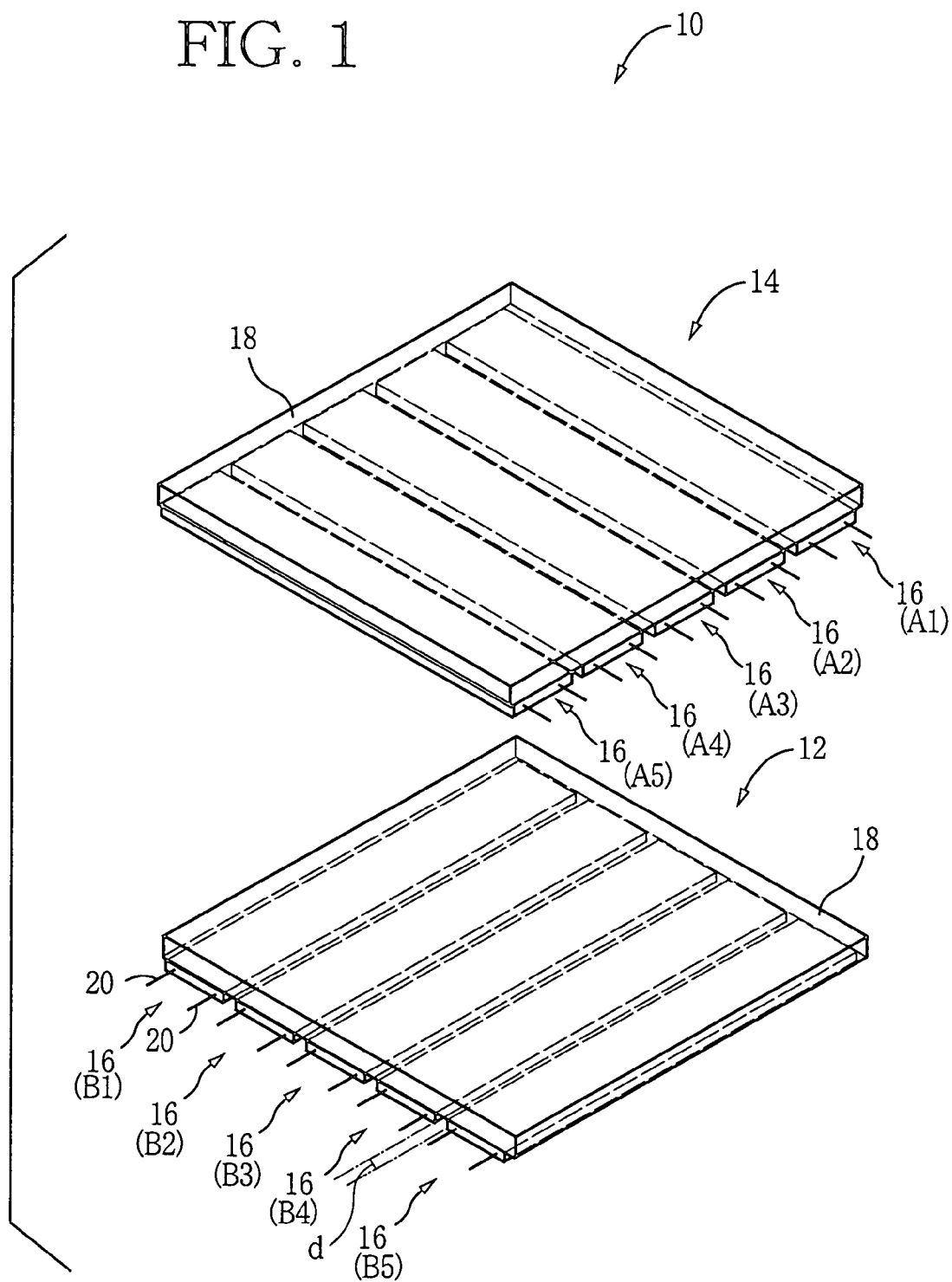
FIG. 1 is a perspective view for explaining a construction of a pressure pulse wave sensor to which the present invention is applied.

Hereinafter, there will be described in detail an embodiment of the present invention by reference to the drawings. FIG. 1 is a perspective view for explaining a construction of a pressure pulse wave sensor 10 to which the present invention is applied.

As shown in FIG. 1, the pressure pulse wave sensor 10 includes a first sensing portion 12, and a second sensing portion 14 having a construction identical with that of the first sensing portion 12. The first sensing portion 12 includes a plurality of belt-like piezoelectric sheets 16 (e.g., five sheets in FIG. 1) that are arranged in a widthwise direction thereof such that the sheets 16 extend parallel to each other. The first sensing portion 12 further includes a flexible sheet 18 having a substantially square shape in its plan view, and the five piezoelectric sheets 16 are adhered to the flexible sheet 18 so as to be integral therewith. The piezoelectric sheets 16 are spaced from each other by a regular distance, d, that is sufficiently smaller than the widthwise dimension of each sheet 16, so that each sheet 16 is prevented from cross-talking with the other sheets 16. Thus, the flexible sheet 18 is expansible and contractible. The flexible sheet 18 is formed of, e.g., vinyl chloride.

Each piezoelectric sheet 16 is formed of a well known piezoelectric polymer such as polyvinylidene fluoride, copolymer of polyvinylidene fluoride and trifluoroethylene, or copolymer of polyvinylidene fluoride and tetrafluoroethylene. Thus, the piezoelectric sheet 16 is given such a flexibility or softness that prevents the sheet 16 against brittle fracture. The flexible sheet 18 is formed of a material that has such a softness that prevents the sheet 18 against brittle fracture, and additionally has some degree of stretchability.

Figure 2:
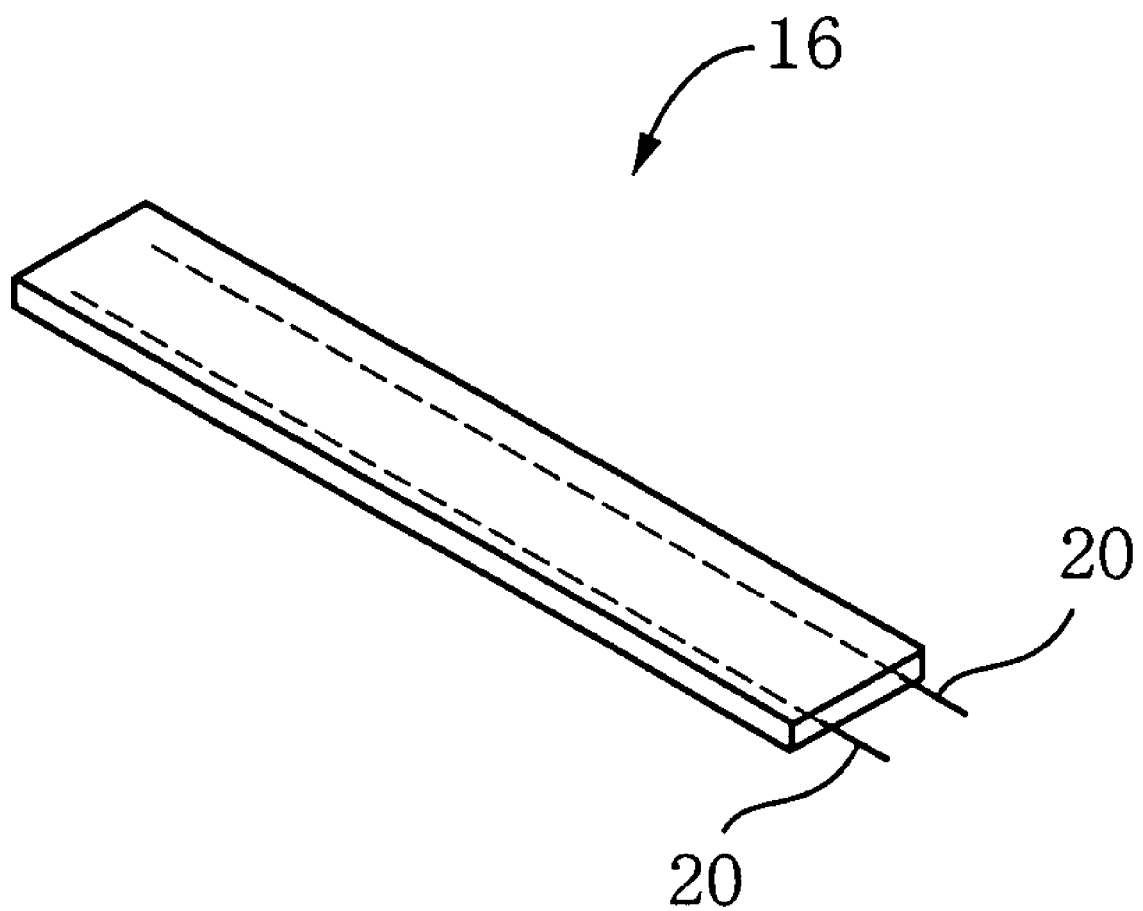
FIG. 2 is a perspective view of one of piezoelectric sheets employed by the pressure pulse wave sensor of FIG. 1.

A pair of electrodes 20 are embedded in each piezoelectric sheet 16. As shown in FIG. 2, the electrodes 20 extend in a lengthwise direction of the sheet 16 from one of lengthwise opposite side surfaces thereof to a portion thereof in the vicinity of the other side surface thereof.

Though the second sensing portion 14 has the same construction as that of the first sensing portion 12, the second sensing portion 14 has an angular position that is deviated from that of the first sensing portion 12 by 90 degrees in a horizontal plane, so that the piezoelectric sheets 16 of the second sensing portion 14 extend perpendicularly to the piezoelectric sheets 16 of the first sensing portion 12. In this state, the second sensing portion 14 is stacked on the first sensing portion 12, and respective lower surfaces of the piezoelectric sheets 16 of the second sensing portion 14 are adhered to an upper surface of the flexible sheet 18 of the first sensing portion 12 (i.e., a surface of the sheet 18 that is opposite to the surface thereof to which the piezoelectric sheets 16 are fixed). Thus, the pressure pulse wave sensor 10 is provided.

The pressure pulse wave sensor 10 constructed as described above may be worn on a living subject, by adhesion with an adhesive compound that is usually used to adhere electrodes of an electrocardiograph to a living being, or by fixing with a band that is wound around a prescribed portion of the subject with the sensor 10 being placed on the prescribed portion. In the state in which the pressure pulse wave sensor 10 is worn on a prescribed portion, such as a wrist, of a living subject, a pressure pulse wave, such as a radial-artery pulse wave, that is produced in the body portion and is transmitted to a surface of the body portion, causes a displacement of each of the piezoelectric sheets 16 and consequently a potential difference corresponding to the displacement, i.e., the pressure pulse wave transmitted to the each piezoelectric sheet 16 is generated between the two electrodes 20 of the each sheet 16.

Figure 3A:
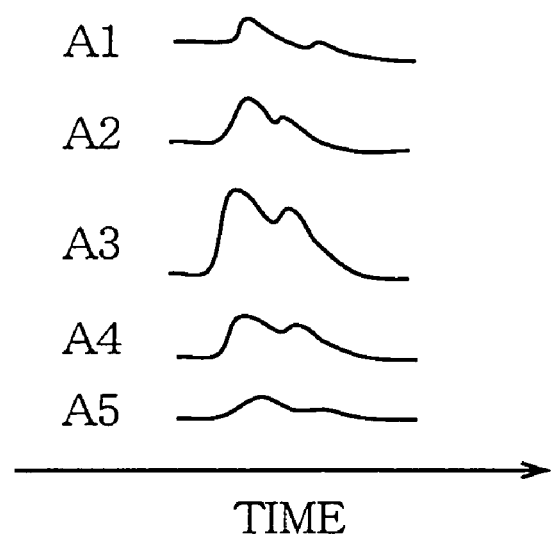
FIG. 3A is a view showing respective pressure pulse waves detected by the piezoelectric sheets employed by a second sensing portion of the pressure pulse wave sensor.
Figure 3B:
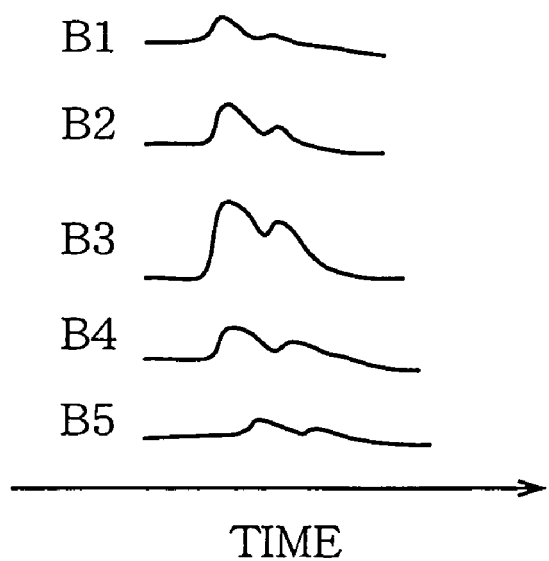
FIG. 3B is a view showing respective pressure pulse waves detected by the piezoelectric sheets employed by a first sensing portion of the pressure pulse wave sensor.

FIGS. 3A and 3B show an example of a pressure pulse wave detected by the pressure pulse wave sensor 10. More specifically described, FIG. 3A shows respective pressure pulse waves detected by the piezoelectric sheets 16 of the second sensing portion 14; and FIG. 3B shows respective pressure pulse waves detected by the piezoelectric sheets 16 of the first sensing portion 12. Symbols A1, . . . , A5, B1, . . . , B5 shown in FIG. 3 represent the respective piezoelectric sheets 16 (A1, . . . , A5, B1, . . . , B5) shown in FIG. 1.

As shown in FIGS. 3A and 3B, the piezoelectric sheets 16 of the pressure pulse wave sensor 10 shown in FIG. 1 detect respective pressure pulse waves. One of the respective pressure pulse waves that has the greatest amplitude of the respective amplitudes of those pressure pulse waves is detected by one of the piezoelectric sheets 16 that is the nearest to a position on the body surface that is right above a pulse-wave producing portion in the subject. For example, regarding the example shown in FIGS. 3A and 3B, each of the pressure pulse waves detected by the piezoelectric sheets A3, B3 contains the greatest amount of target-pulse-wave component. Therefore, when a pressure pulse wave detected by the pressure pulse wave sensor 10 is used in making a diagnosis on the subject, the most reliable diagnosis can be obtained, regarding the example shown in FIGS. 3A and 3B, by using the pressure pulse waves detected by the piezoelectric sheets A3, B3.

Figure 4:
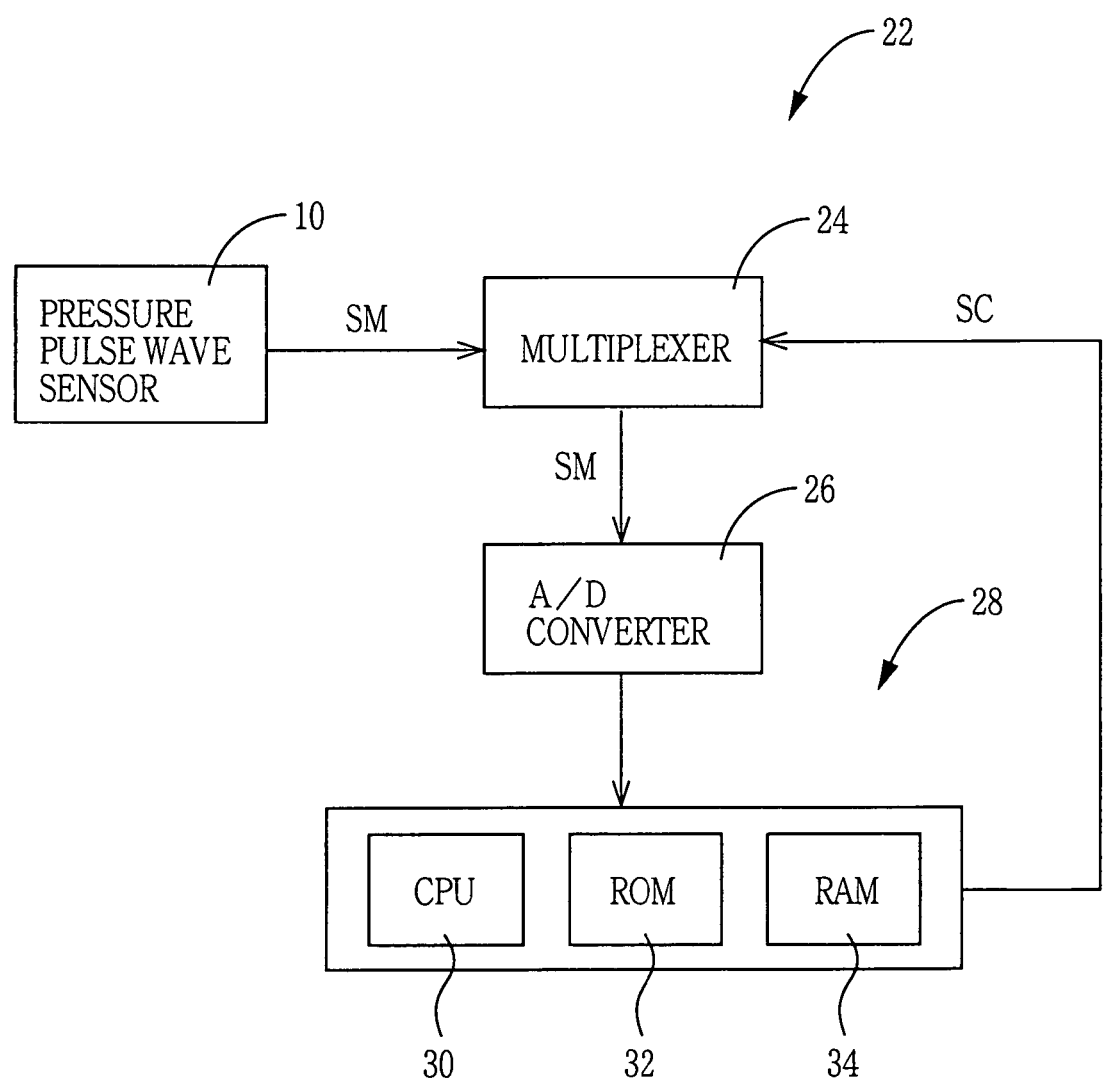
FIG. 4 is a diagrammatic view for explaining a construction of a pressure-pulse-wave analyzing apparatus employing the pressure pulse wave sensor.

FIG. 4 is a diagrammatic view for explaining a construction of a pressure-pulse-wave analyzing apparatus 22 employing the pressure pulse wave sensor 10. The pressure-pulse-wave analyzing apparatus 22 includes, in addition to the pressure pulse wave sensor 10, a multiplexer 24, an A/D (analog-to-digital converter) 26, and an electronic control device 28. The analyzing apparatus 22 may be employed by an apparatus that makes a diagnosis on a patient based on a form of a pulse wave detected from the patient, or by an apparatus that determines a characteristic point, such as a rising point or a peak point, of a pulse wave detected from a patient, so as to determine a pulse-wave propagation velocity and make a diagnosis on the patient based on the propagation velocity.

In the state in which the pressure pulse wave sensor 10 is worn on the prescribed portion of the subject, each of the piezoelectric sheets 16 of the sensor 10 outputs a pulse-wave signal SM representing a pressure pulse wave that is produced from the body portion and is transmitted to the surface of the body portion. The multiplexer 24 supplies, according to respective switch signals SC supplied thereto from the electronic control device 28, the respective pulse-wave signals SM outputted by the ten piezoelectric sheets 16 of the sensor 10, one by one, to the A/D converter 26, each for a prescribed time duration. The A/D converter 26 converts each of the pulse-wave signals SM sequentially supplied thereto from the multiplexer 24, into a digital signal, and supplies the digital signals to the control device 28.

The electronic control device 28 is provided by a so-called microcomputer including a CPU (central processing unit) 30, a ROM (read only memory) 32, a RAM (random access memory) 34, and an I/O (input-and-output) port, not shown. The CPU 30 processes signals according to the control programs pre-stored in the ROM 32 by utilizing the temporary-storage function of the RAM 34, and reads in the respective pressure pulse waves detected by all the piezoelectric sheets 16 of the pressure pulse wave sensor 10, determines one of the respective pressure pulse waves detected by the respective piezoelectric sheets 16 of the first sensing portion 12 that has the greatest amplitude (hereinafter, referred to as the first greatest-amplitude pulse wave), determines one of the respective pressure pulse waves detected by the respective piezoelectric sheets 16 of the second sensing portion 14 that has the greatest amplitude (hereinafter, referred to as the second greatest-amplitude pulse wave), removes noise from each of the first and second greatest-amplitude pulse waves, and synthesizes a pulse wave based on the first and second greatest-amplitude pulse waves from which noise has been removed.

Figure 5:
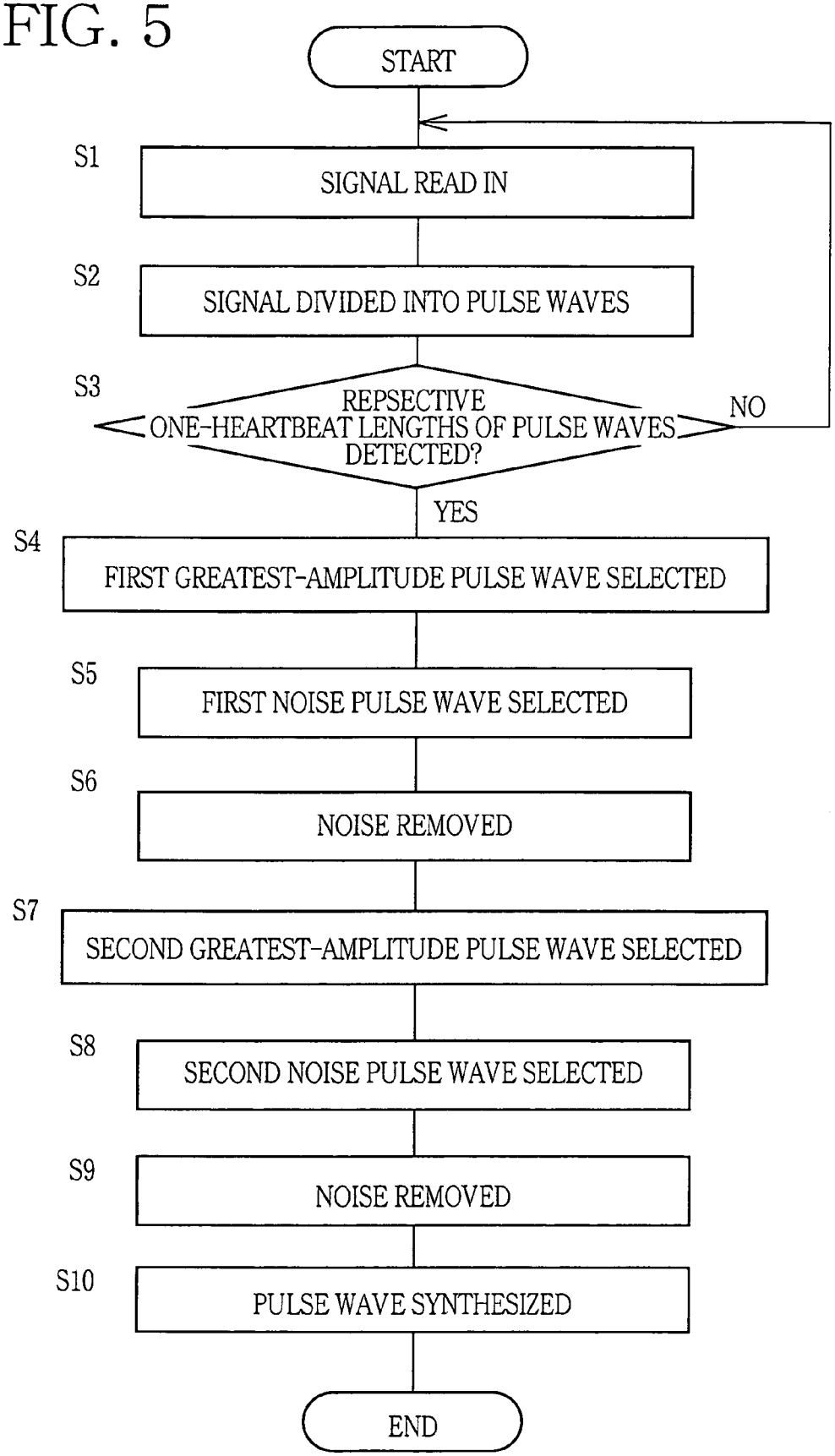
FIG. 5 is a flow chart for explaining essential control functions of a CPU (central processing unit) shown in FIG. 4.

FIG. 5 is a flow chart representing essential control functions of the CPU 30. In FIG. 5, first, the CPU carries out Step S1 (hereinafter, "Step" is omitted) to read in, at a pre-set sampling period, the pulse-wave signal SM supplied from the A/D converter 26. Subsequently, at S2, the CPU divides, based on the switching period SC, the pulse-wave signal SM read in at S1, into the respective pulse waves detected by the piezoelectric sheets 16 of the pressure pulse wave sensor 10. Then, at S3, the CPU judges whether respective one-heartbeat lengths of the respective pulse waves have been obtained.

If a negative judgment is made at S3, then the CPU repeats S1 and the following steps. On the other hand, if a positive judgment is made at S3, the control of the CPU goes to S4 to determine, as the first greatest-amplitude pulse wave, one of the respective one-heartbeat lengths of the respective pulse waves detected by the piezoelectric sheets 16 of the first sensing portion 12 that has the greatest amplitude. For example, regarding the five pulse waves shown in FIG. 3B, the CPU determines, as the first greatest-amplitude pulse wave, the one-heartbeat length of the pulse wave detected by the piezoelectric sheet B3. It can be said that the first greatest-amplitude pulse wave is detected by one of the piezoelectric sheets 16 of the first sensing portion 12 that is located at a position right above a target-signal producing portion, such as an artery, and contains the greatest amount of component that represents a target pulse wave produced by the artery.

Subsequently, at S5, the CPU determines the pulse wave detected by one of the piezoelectric sheets 16 of the first sensing portion 12 that is the most distant from the piezoelectric sheet 16 detecting the first greatest-amplitude pulse wave, as a pulse wave that contains the greatest amount of noise of the respective amounts of noise contained by the respective pulse waves detected by the piezoelectric sheets 16 of the first sensing portion 12 (hereinafter, referred to as "the first noise pulse wave"). Since noise such as motion of a muscle is similarly detected in a wide range, the respective pulse waves detected by the respective piezoelectric sheets 16 contain a similar amount of noise. However, the magnitude of the target signal decreases as the signal travels further away from the target-signal producing portion. Thus, it can be said that the pulse wave detected by the piezoelectric sheet 16 that is the most distant from the piezoelectric sheet 16 detecting the first greatest-amplitude pulse wave contains the greatest amount of noise. For example, regarding the example shown in FIG. 3B, the CPU determines, as the first noise pulse wave, one of the respective one-heartbeat lengths of the pulse waves detected by the piezoelectric sheets B1, B5. Thus, the two candidates for the first noise pulse wave have been determined based on the distances between the respective pairs of piezoelectric sheets 16. In this case, the CPU determines, as the first noise pulse wave, one of the candidate pulse waves according to a prescribed condition other than the distances between the respective pairs of piezoelectric sheets 16. For example, the CPU determines, as the first noise pulse wave, one of the candidate pulse waves that has the smaller amplitude.

Subsequently, at S6, the CPU subtracts the amplitude of the first noise pulse wave determined at S5, from the greatest amplitude of the first greatest-amplitude pulse wave determined at S4, so as to remove, from the first greatest-amplitude pulse wave, the noise component other than the target-signal component.

Then, at S7 through S9, the CPU similarly determines, for the second sensing portion 14, the second greatest-amplitude pulse wave having the greatest amplitude, and the second noise pulse wave containing the greatest amount of noise.

More specifically described, first, at S7, the CPU determines, as the second greatest-amplitude pulse wave, one of the respective one-heartbeat lengths of the respective pulse waves detected by the piezoelectric sheets 16 of the second sensing portion 14 that has the greatest amplitude. For example, regarding the five pulse waves shown in FIG. 3A, the CPU determines, as the second greatest-amplitude pulse wave, the one-heartbeat length of the pulse wave detected by the piezoelectric sheet A3. Subsequently, at S8, the CPU determines the one-heartbeat length of the pulse wave detected by one of the piezoelectric sheets 16 of the second sensing portion 14 that is the most distant from the piezoelectric sheet 16 detecting the second greatest-amplitude pulse wave, as a pulse wave that contains the greatest amount of noise of the respective amounts of noise contained by the respective pulse waves detected by the piezoelectric sheets 16 of the second sensing portion 14 (hereinafter, referred to as "the second noise pulse wave"). If two candidates for the second noise pulse wave have been determined based on the distances between the respective pairs of piezoelectric sheets 16, the CPU determines, as the second noise pulse wave, one of the candidate pulse waves according to a prescribed condition other than the distances between the respective pairs of piezoelectric sheets 16, in the same manner as the manner in which the CPU determines the first noise pulse wave. For example, the CPU determines, as the second noise pulse wave, one of the candidate pulse waves that has the smaller amplitude. In the flow chart shown in FIG. 5, S4 through S9 correspond to a noise removing device or means.

Subsequently, the control goes to S10 corresponding to a pulse-wave synthesizing device or means. At S10, the CPU synthesizes a synthetic pulse wave based on the first greatest-amplitude pulse wave from which noise has been removed at S6, and the second greatest-amplitude pulse wave from which noise has been removed at S9. For example, the CPU may synthesize a synthetic pulse wave by adding the first and second greatest-amplitude pulse waves to each other and dividing the thus obtained pulse wave by 2, i.e., averaging the two pulse waves, or multiplying the two pulse waves by each other. The synthetic pulse wave synthesized by averaging the two pulse waves accurately represents the target-signal component, whereas the synthetic pulse wave synthesized by multiplying the two pulse waves emphasizes a characteristic point, such as a peak point, of the target signal component. Thus, the latter synthetic pulse wave does not represent the form of the target signal component so accurately as the former synthetic pulse wave does, but more clearly shows the characteristic point of the target signal component. Thus, the CPU can synthesize a synthetic pulse wave based on the two greatest-amplitude pulse waves, in a selected one of various manners that is appropriate for the application of the synthetic pulse wave.

In the above-described pressure pulse wave sensor 10, the piezoelectric sheets 16 are flexible and are integrally fixed to the flexible sheet 18. Therefore, the piezoelectric sheets 16 can be worn on the body surface in the state in which the sheets 16 fit the curved shape of the body surface. Thus, each of the piezoelectric sheets 16 can detect a pressure pulse wave that accurately represents the displacement of the body surface. On the other hand, a single large piezoelectric sheet having a large area equal to an area defined by the piezoelectric sheets 16 connected to each other, detects a pulse wave representing a total amount of displacement of the large area. In the latter case, the pulse wave detected is likely to represent other displacements than the pulse wave produced by the target-signal producing portion. In contrast, the pressure pulse wave sensor 10 employs the elongate piezoelectric sheets 16 arranged in the widthwise direction thereof, and accordingly each of the piezoelectric sheets 16 detects the displacement of the narrower area than the single large piezoelectric sheet does. Therefore, the piezoelectric sheet 16 located at the position right above the pulse-wave producing portion can detect the pulse wave that more accurately represents the target pulse wave produced by the target-signal producing portion.

In addition, the flexible sheet 18 of the pressure pulse wave sensor 10 is expansible and contractible and accordingly the flexible sheet 18 easily fits the curved shape of the body surface. Thus, the piezoelectric sheets 16 that are fixed to the flexible sheet 18 and are pressed against the body surface more suitably fit the curved shape of the body surface. Therefore, each of the piezoelectric sheets 16 can detect an accurate pressure pulse wave.

The pressure-pulse-wave analyzing apparatus 22 synthesizes a synthetic pulse wave based on the first greatest-amplitude pulse wave containing the greatest amount of target-signal component of the respective amounts of target-signal components contained by the respective pulse waves detected by the piezoelectric sheets 16 of the first sensing portion 12, and the second greatest-amplitude pulse wave containing the greatest amount of target-signal component of the respective amounts of target-signal components contained by the respective pulse waves detected by the piezoelectric sheets 16 of the second sensing portion 14. Therefore, the synthetic pulse wave accurately represents the target pulse wave.

In addition, the pressure-pulse-wave analyzing apparatus 22 subtracts, from the first and second greatest-amplitude pulse waves each containing the greatest amount of target-signal component, the first and second noise pulse waves each containing the greatest amount of noise component, respectively, and synthesizes a synthetic pulse wave based on the first and second greatest-amplitude pulse waves from which noise has been removed. Thus, the synthetic pulse wave accurately represents the target pulse wave.

Figure 6:
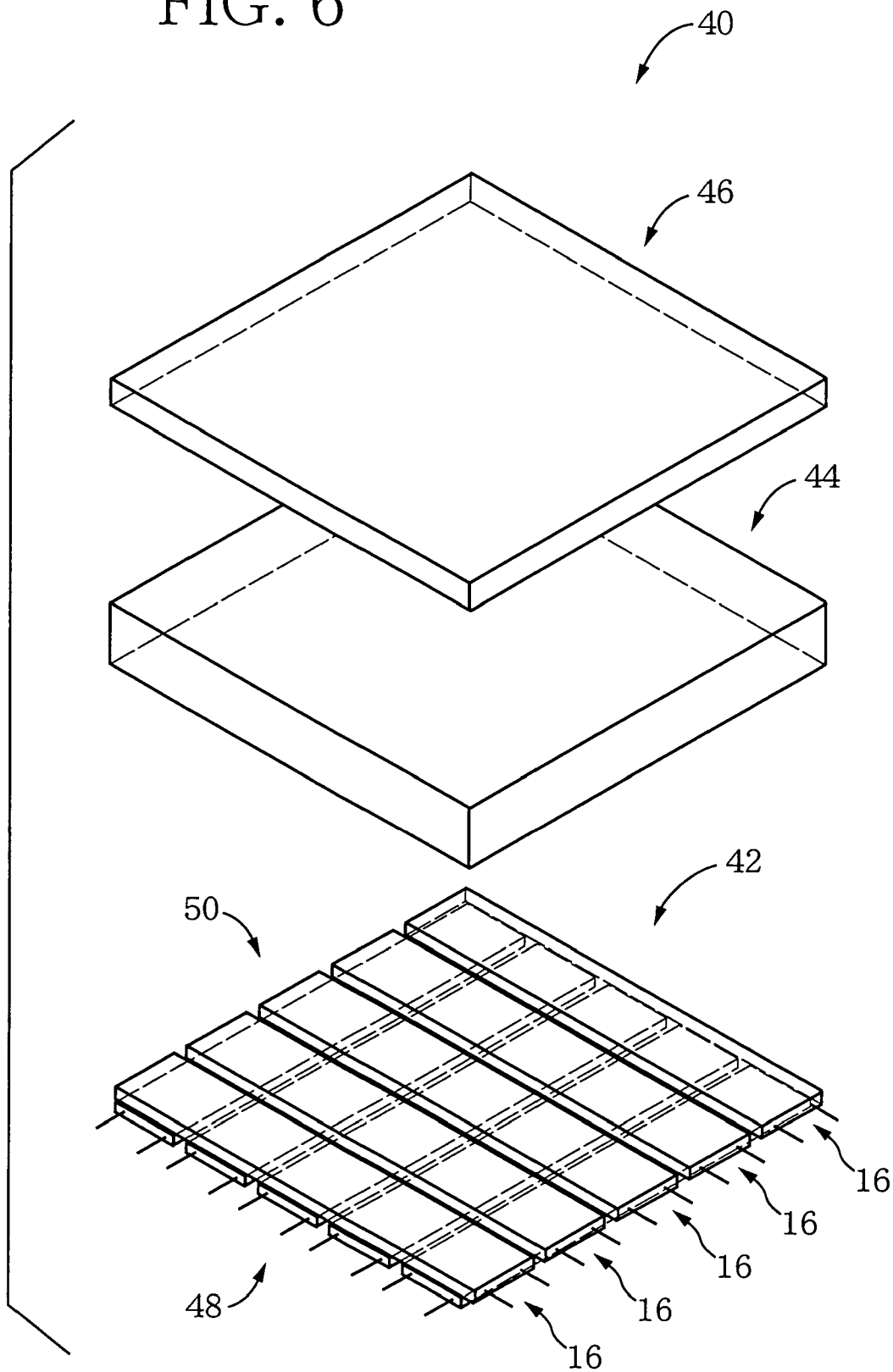
FIG. 6 is a perspective view for explaining a construction of another pressure pulse wave sensor different from the sensor shown in FIG. 1.

Next, there will be described another pressure pulse wave sensor 40 to which the present invention is applied. FIG. 6 is a perspective view for explaining a construction of the pressure pulse wave sensor 40. The pressure pulse wave sensor 40 shown in FIG. 6 includes a sensing portion 42 that has a substantially square shape in its plan view; an elastic base member 44 that has the substantially same shape in its plan view as that of the sensing portion 42; and a considerably hard base plate 46. The sensing portion 42, the basic member 44, and the basic plate 46 are stacked on each other in the order of description, and are adhered to each other so as to be integral with each other.

The sensing portion 42 includes a first sensing portion 48 that has a construction obtained by removing the flexible sheet 18 from the first sensing portion 12 of the pressure pulse wave sensor 10; and a second sensing portion 50 that has the same construction as that of the first sensing portion 48 and has an angular position that is deviated from that of the first sensing portion 48 by 90 degrees in a horizontal plane. The first and second sensing portions 48, 50 are stacked on each other.

The elastic base member 44 that is stacked on an upper surface of the second sensing portion 50 (i.e., a surface of the second sensing portion that is distant from the first sensing portion 48) is formed of an elastic material such as a sponge, a rubber, or a gel, and has a thickness sufficiently greater than that of each piezoelectric sheet 16. The basic plate 46 that is stacked on an upper surface of the elastic base member 44 (i.e., a surface of the elastic base member that is distant from the second sensing portion 50) is formed of a hard resin so as to minimize elastic deformation thereof, and has a thickness sufficiently greater than that of each piezoelectric sheet 16.

Figure 7:
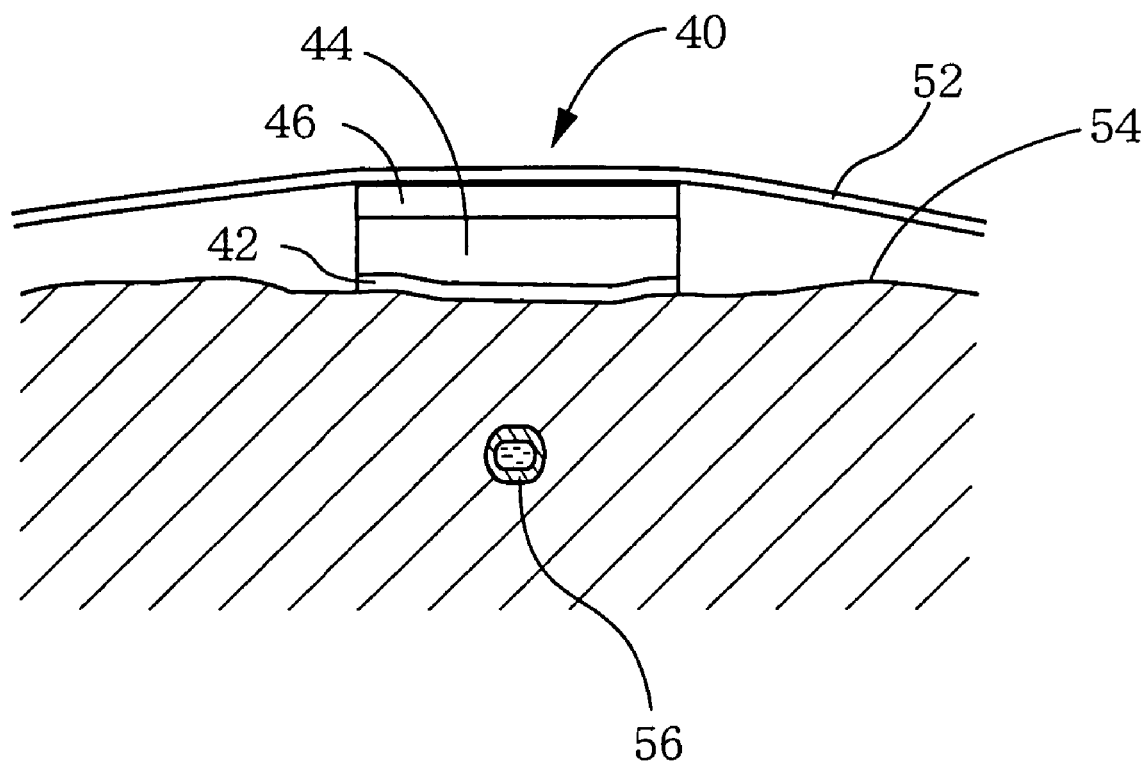
FIG. 7 is a view showing a state in which the pressure pulse wave sensor shown in FIG. 6 is worn on a prescribed region of a living being.

FIG. 7 shows a state in which the pressure pulse wave sensor 40 is worn on a surface of a prescribed portion of a living subject. The pressure pulse wave sensor 40 is worn on the prescribed portion of the subject, with a fixing band 52. In the state in which the pressure pulse wave sensor 40 is fixed with the fixing band 52, the piezoelectric sheets 16 of the sensing portion 42 are pressed against a body surface 54 of the subject and each of the piezoelectric sheets 16 detects a displacement that is produced from an artery 56 and is transmitted to the body surface 54, and a change in pressure in the tissue of the subject.

In the pressure pulse wave sensor 40, each of the piezoelectric sheets 16 is flexible. In the state in which the pressure pulse wave sensor 40 is fixed on the body surface 54, each of the piezoelectric sheets 16 is pressed toward the body surface 54 by an elastic shape recovery force of the elastic base member 44. Thus, each piezoelectric sheet 16 fits the curved shape of the body surface 54. Therefore, each piezoelectric sheet 16 detects a pulse wave accurately representing the displacement of the body surface 54 and the change in pressure in the subject's tissue. On the other hand, a single large piezoelectric sheet having a large area equal to an area defined by the piezoelectric sheets 16 connected to each other, detects a pulse wave representing a total amount of displacement of the large area. In the latter case, the pulse wave detected is likely to represent other displacements than the pulse wave produced by the target-signal producing portion. In contrast, the pressure pulse wave sensor 40 employs the elongate piezoelectric sheets 16 arranged in the widthwise direction thereof, and accordingly each of the piezoelectric sheets 16 detects the displacement of the narrower area than the single large piezoelectric sheet does. Therefore, the piezoelectric sheet 16 located at the position right above the pulse-wave producing portion (i.e., the artery 56) can detect the pulse wave that more accurately represents the target pulse wave produced by the target artery 56.

In another embodiment of the present invention, the pressure pulse wave sensor 10 employed by the pressure pulse wave analyzing apparatus 22 shown in FIG. 4 is replaced with the pressure pulse wave sensor 40 shown in FIG. 6. In this embodiment, S7 through S10 of the flow chart shown in FIG. 5 are omitted.

While the present invention has been described in its embodiments by reference to the drawings, it is to be understood that the invention may otherwise be embodied.

For example, each of the piezoelectric sheets 16 has the two electrodes 20 projecting from one of the lengthwise opposite side surfaces thereof. However, each piezoelectric sheet 16 may be so modified as to have two electrodes 20 projecting from upper and lower surfaces thereof.

In the flow chart shown in FIG. 5, after the first and second noise pulse wave are respectively subtracted from the first and second greatest-amplitude pulse waves respectively determined at S4 and S7, so as to remove noise from the first and second greatest-amplitude pulse waves, the synthetic pulse wave is produced based on the first and second greatest-amplitude pulse waves. However, in the case where the noise component is not so important in making a diagnosis, a pulse wave may be directly synthesized based on the first and second greatest-amplitude pulse waves determined at S4 and S7.

In the flow chart shown in FIG. 5, the first or second noise pulse wave used to remove noise from the first or second greatest-amplitude pulse wave is obtained from the piezoelectric sheet 16 that is the most distant from the piezoelectric sheet 16 detecting the first or second greatest-amplitude pulse wave. However, it can be said that the respective pulse waves detected by all the piezoelectric sheets 16 uniformly contain the noise component. Therefore, a pulse wave detected by a different piezoelectric sheet 16 than the most distant piezoelectric sheet 16 may be used as the first or second noise pulse wave to be subtracted from the first or second greatest-amplitude pulse wave.

In the pressure pulse wave sensor 10, the upper surface of the flexible sheet 18 of the first sensing portion 12 and the lower surfaces of the piezoelectric sheets 16 of the second sensing portion 14 are adhered to each other. However, a sheet having a low friction coefficient may be interposed between those surfaces being not adhered to each other. In the latter case, noise produced by friction between the first and second sensing portions 12, 14 is reduced and accordingly noise contained in the pulse wave detected by each piezoelectric sheet 16 is reduced.

While the present invention has been described in its embodiments in detail by reference to the drawings, it may be understood that the present invention is by no means limited to the details of the embodiments but may be embodied with various changes and improvements that may occur to a person skilled in the art.

What is claimed is:

1. A pressure-pulse-wave analyzing apparatus, comprising:
    a pressure pulse wave sensor which is adapted to be worn on a surface of a body of a living subject so as to detect a pressure pulse wave from the subject and which comprises a first sensing portion including a plurality of elongate flexible piezoelectric sheets each of which is formed of a piezoelectric resin and detects a first pressure pulse wave from the subject and which are arranged in a widthwise direction thereof, and a second sensing portion including a plurality of elongate flexible piezoelectric sheets each of which is formed of a piezoelectric resin and detects a second pressure pulse wave from the subject and which are arranged in a widthwise direction thereof, the second sensing portion being stacked on the first sensing portion such that the piezoelectric sheets of the second sensing portion extend perpendicularly to the piezoelectric sheets of the first sensing portion; and
    a synthesizing means for synthesizing a synthetic pulse wave based on one of the respective first pressure pulse waves detected by the piezoelectric sheets of the first sensing portion that has a greatest amplitude of respective amplitudes of the first pressure pulse waves, and one of the respective second pressure pulse waves detected by the piezoelectric sheets of the second sensing portion that has a greatest amplitude of respective amplitudes of the second pressure pulse waves.

2. A pressure-pulse-wave analyzing apparatus according to claim 1, further comprising a noise removing means for subtracting, from said one first pressure pulse wave having the greatest amplitude, a different one of the first pressure pulse waves that is different from said one first pressure pulse wave, and thereby removing noise from said one first pressure pulse wave, and subtracting, from said one second pressure pulse wave having the greatest amplitude, a different one of the second pressure pulse waves that is different from said one second pressure pulse wave, and thereby removing noise from said one second pressure pulse wave, wherein the synthesizing means synthesizes the synthetic pulse wave based on said one first pressure pulse wave from which noise has been removed by the noise removing means and said one second pressure pulse wave from which noise has been removed by the noise removing means.

3. A pressure-pulse-wave analyzing apparatus, comprising:
    a pressure pulse wave sensor which is adapted to be worn on a surface of a body of a living subject so as to detect a pressure pulse wave from the subject and which comprises a first sensing portion including a plurality of elongate flexible piezoelectric sheets each of which is formed of a piezoelectric resin and detects a first pressure pulse wave from the subject and which are arranged in a widthwise direction thereof, and a second sensing portion including a plurality of elongate flexible piezoelectric sheets each of which is formed of a piezoelectric resin and detects a second pressure pulse wave from the subject and which are arranged in a widthwise direction thereof, the second sensing portion being stacked on the first sensing portion such that the piezoelectric sheets of the second sensing portion extend perpendicularly to the piezoelectric sheets of the first sensing portion; and
    a synthesizing device which synthesizes a synthetic pulse wave based on one of the respective first pressure pulse waves detected by the piezoelectric sheets of the first sensing portion that has a greatest amplitude of respective amplitudes of the first pressure pulse waves, and one of the respective second pressure pulse waves detected by the piezoelectric sheets of the second sensing portion that has a greatest amplitude of respective amplitudes of the second pressure pulse waves.

* * * * *